United States Patent [19]

Parins

[11] Patent Number: 5,197,963
[45] Date of Patent: Mar. 30, 1993

[54] ELECTROSURGICAL INSTRUMENT WITH EXTENDABLE SHEATH FOR IRRIGATION AND ASPIRATION

[75] Inventor: David J. Parins, Columbia Heights, Minn.

[73] Assignee: Everest Medical Corporation, Minneapolis, Minn.

[21] Appl. No.: 801,385

[22] Filed: Dec. 2, 1991

[51] Int. Cl.[5] ............................................. A61B 17/36
[52] U.S. Cl. ..................................... 606/46; 606/41; 606/48; 606/50; 128/784; 128/786
[58] Field of Search ..................... 606/41, 43, 45, 46, 606/49, 37, 36, 39, 40, 44, 48, 50, 51, 52; 128/783, 784, 800; 604/22

[56] References Cited

U.S. PATENT DOCUMENTS

| | | | |
|---|---|---|---|
| 2,275,167 | 3/1942 | Bierman | 606/49 X |
| 4,049,000 | 9/1977 | Williams | 604/119 |
| 4,362,160 | 12/1982 | Hiltebrandt | 606/46 |
| 4,911,159 | 3/1990 | Johnson et al. | 606/45 X |
| 4,919,129 | 4/1990 | Weber, Jr. et al. | 606/45 X |
| 5,071,418 | 12/1991 | Rosenbaum | 606/45 X |

*Primary Examiner*—Stephen C. Pellegrino
*Assistant Examiner*—Jeffrey A. Schmidt
*Attorney, Agent, or Firm*—Haugen and Nikolai

[57] ABSTRACT

An electrosurgical instrument having a protective, extendable and retractable sheath or sleeve is disclosed. The sheath is disposed around and coaligned with an elongated cylindrical rod, from which extends at least one electrode. A conductor extending from the electrode is joined to a conventional power supply cord for connection to a source of RF voltage. Power supply is regulated using either a convention hand or foot switch. The sheath protects the distal electrode(s) as the instrument is inserted through a laparoscopic trocar or endoscope. It also provides an effective extension of an irrigation/aspiration lumen which extends along the length of the cylindrical rod. The proximal end of the irrigation/aspiration lumen is joined to a supply tube which either may be connected to a fluid reservoir for irrigation or to a collection reservoir for aspiration of fluids. Alternative embodiments feature alternative mechanisms for extending the sheath. In one embodiment, the sheath is retractable and shields the electrode(s) only when placed in a distal, extended position. In another embodiment, the cylindrical rod-shaped housing on which the electrode resides is retractable. When the cylindrical rod is withdrawn to a proximal, retracted position with the sheath, it shields the electrode and extends the effective end of the irrigation lumen.

15 Claims, 1 Drawing Sheet

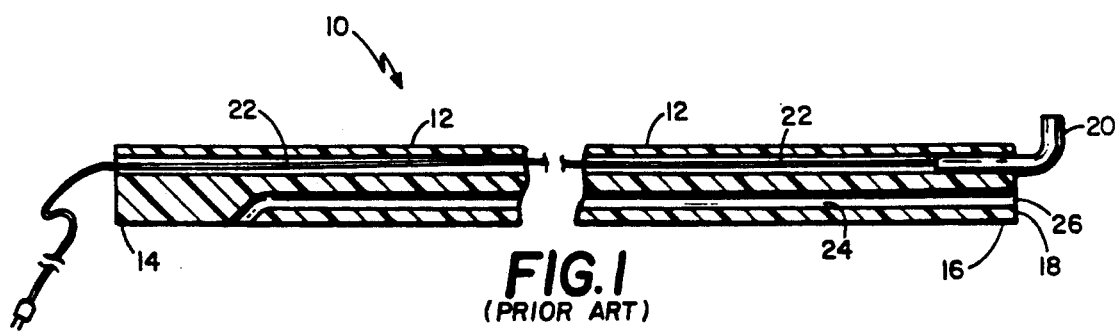
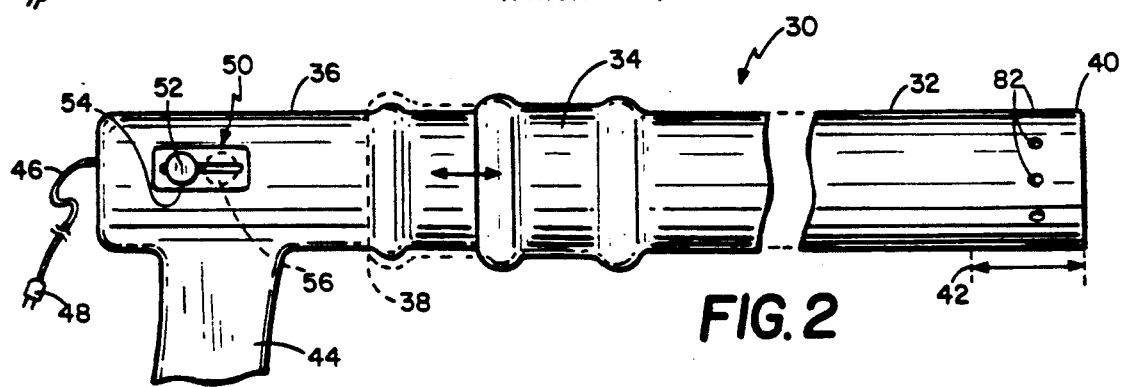
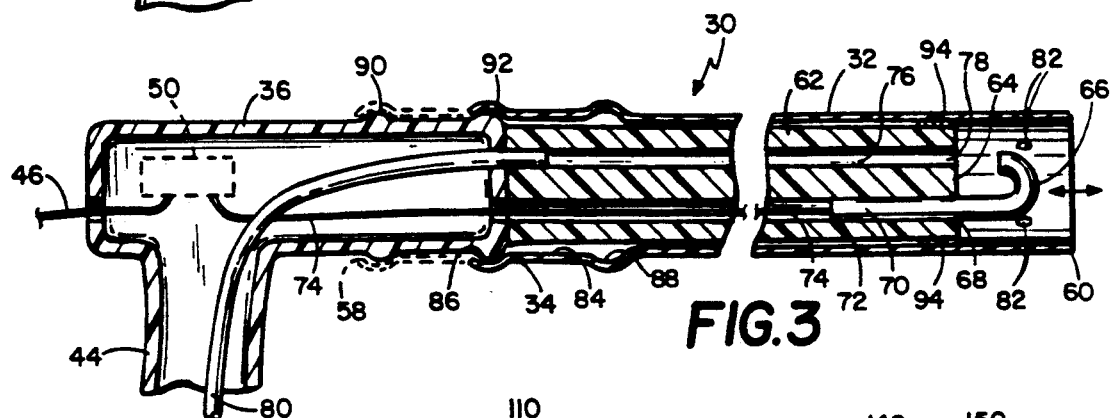
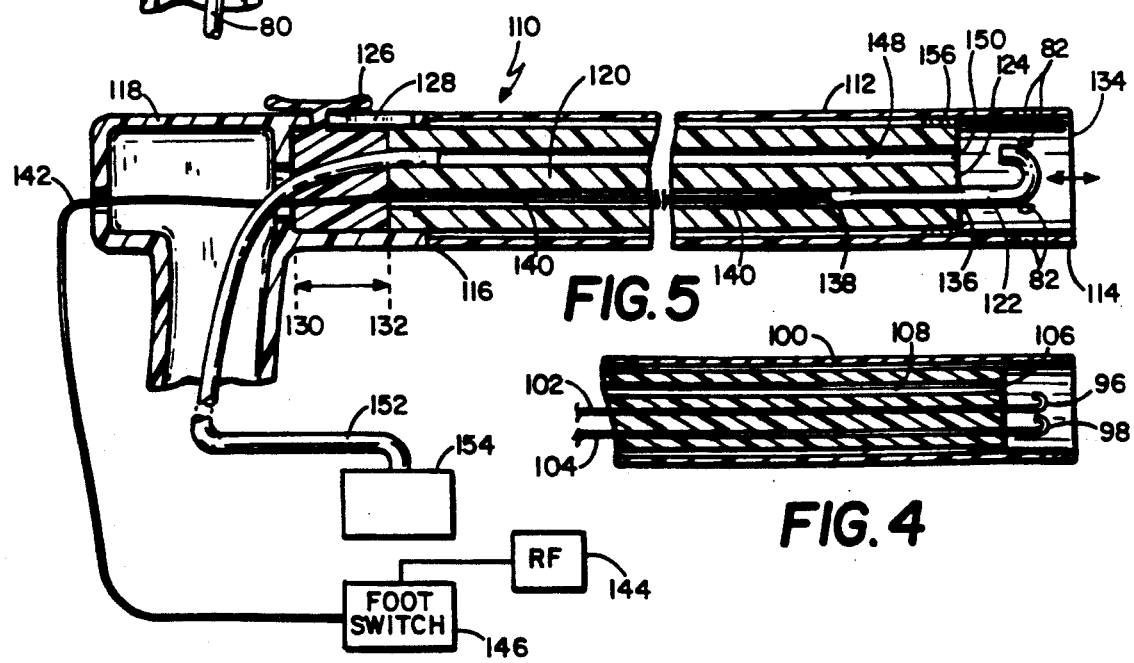

ELECTROSURGICAL INSTRUMENT WITH EXTENDABLE SHEATH FOR IRRIGATION AND ASPIRATION

BACKGROUND OF THE INVENTION

1. Field of the Invention

This invention relates generally to the design of electrosurgical instruments and more particularly to a monopolar or bipolar electrosurgical instrument having an extendable lumen which permits selective irrigation and aspiration of the treatment region. In one embodiment, a sheath is reciprocally moveable in relation to the main housing of the electrosurgical instrument and features at least one pressure release port at its distal end to reduce the amount of suction provided to tissue. In an alternative embodiment, a tubular housing having at least one distal electrode extending therefrom is reciprocally movable within a stationary, external sleeve.

2. Discussion of the Prior Art

Monopolar and bipolar electrosurgical instruments typically include an electrode extending from a distal end of a rigid or flexible tube. In these instruments, it is desirable to include a lumen with a distal exit port positioned near the electrodes to supply irrigation fluid and to aspirate that fluid and debris from the region. Although electrodes used on these instruments are configured for optimal contact with tissue, the fact that they generally project outwards makes it difficult to manipulate the distal end of the device to position an irrigation/aspiration port adjacent to tissue, in order to selectively flush one area of a treatment region or to aspirate blood or bodily fluids from the region. Although it is common to include a suction or irrigation lumen within such instruments, the port is often displaced too far from tissue to be optimally effective. This obstruction occurs even when the electrodes are specially dimensioned to enhance irrigation and aspiration. Furthermore, these instruments are typically inserted through the lumen of a laparoscopic trocar or endoscope, within which the protruding electrodes may be damaged as the instrument is negotiated through bends and curves in the lumen.

The present invention solves these problems presented in the prior art by providing a retractable or extendable sleeve or sheath which may be extended distally in relation to the surface holding the electrodes and which, when extended, encompasses the electrode housing and electrodes of the electrosurgical instrument. When extended, the sleeve protects the electrodes during insertion and also functions as an extension of the suction and irrigation port. Thus, when extended, the point at which suction takes place is provided closer to the actual treatment site than was possible using prior art instruments. Alternatively, the housing on which the electrodes are mounted may be retracted into a stationary sleeve, again enabling the orifice of the irrigation/aspiration tube to be effectively placed nearer a treatment region than was possible in the prior art.

It is accordingly a principal object of the present invention to provide a new and improved electrosurgical instrument for insertion into a laparoscopic trocar or endoscope.

Another object of the present invention is to provide a new and improved apparatus for irrigation and aspiration of a treatment region featuring a retractable and extendable sheath to enable application of irrigation and aspiration nearer a treatment region.

It is yet another object of the present invention to provide a new and improved apparatus for irrigation and aspiration of a treatment region featuring a retractable and extendable electrode housing which may be withdrawn into a stationary sheath to enable application of irrigation and aspiration nearer a treatment region.

A further object of the present invention is to provide a new and improved apparatus for attaining a level of controlled suction which will not damage tissue by grasping it too strongly.

A still further object of the present invention is to provide a new and improved apparatus having a sheath which acts as a protective sleeve as the instrument is inserted through a laparoscopic trocar or endoscope.

SUMMARY OF THE INVENTION

The present invention provides an electrosurgical instrument having an extendable protective sleeve or sheath which encompasses the distal end of the instrument to protect its electrodes as the instrument is fed through a laparoscopic trocar or endoscope and to provide an effective extension of an irrigation/aspiration lumen. Extension of this sheath in the distal direction moves it to a position which encompasses or shields the electrodes. Extension of the sheath also provides a tube through which irrigation fluid may be directed or which provides suction at a precise site. Thus, the protruding electrodes no longer interfere with the efficacy of aspiration or irrigation of the treatment region as they do in prior art devices. A plurality of small holes dispensed along the sleeve provide relief during aspiration so that the tissue is not grasped too strongly while being treated.

Alternatively, the housing on which the distal electrodes are mounted may be retracted into a relatively rigid stationary sleeve. In either embodiment, the protruding electrodes no longer interfere with placement of the irrigation/aspiration port into the treatment region.

The aforementioned objects and advantages of the invention will become subsequently apparent and reside in the details of construction and operation as more fully hereinafter described and claimed, reference being had to the accompanying drawings forming a part thereof, wherein like numerals refer to like parts throughout.

DESCRIPTION OF THE DRAWINGS

FIG. 1 shows a cross-sectioned view of a prior art electrosurgical instrument;

FIG. 2 shows a partial, side elevation view of a preferred embodiment of the present invention;

FIG. 3 shows a partial, cross-sectioned side view of the embodiment of FIG. 2;

FIG. 4 shows a partial, cross-sectioned side view of a bipolar electrode distal tip arrangement including the present invention; and FIG. 5 shows a partial, cross-sectioned side view of an alternative embodiment of the present invention.

DESCRIPTION OF THE PREFERRED EMBODIMENT

FIG. 1 shows a partial, cross-sectioned view of a prior art electrosurgical instrument having at least one electrode extending from a distal surface. This electrosurgical instrument, generally depicted as 10, typically includes a tubular member 12 having a proximal end 14 and a distal end 16. Extending from a distal surface 18 is at least one conductive electrode 20 having a flexible conductor means 22 extending from an RF voltage source (not shown). A lumen 24 extends through tubular member 12 and terminates at a distal port 26 in the region of electrode 20 on distal surface 18. The port 26 is used for irrigation and aspiration of the treatment region. Irrigation is necessary to periodically cleanse the treatment region with fluid from a reservoir (not shown). Aspiration is necessary to remove blood and bodily fluids from discrete regions of the tissue surface before treatment can continue. Although placed near electrode 20 in prior art devices, the irrigation/aspiration port 26 is nevertheless generally displaced too far from the tissue to be treated to be optimally effective. In other words, more accurate placement of the irrigation/aspiration port is frequently desired but not attainable due to obstruction caused by the projecting electrodes 20. For example, interference from the projection of the electrode permits only general flushing of the surrounding tissue, not selective flushing of a precise site.

FIG. 2 shows an electrosurgical instrument 30 constructed in accordance with the present invention. It incorporates a protective sheath 32 rigidly affixed to an extender member 34 mounted on a housing 36. Distal and proximal movement of extender member 34 causes sheath 32 to be displaced distally or proximally. Thus, extender member 34 may be displaced proximally, as indicated at 38 (in shadow), to withdraw the distal end 40 of sheath 32 to a proximal position 42. Extending from the underside of housing 36 is a hand grip 44 enclosing a tubular aspiration/irrigation member (FIG. 3). Extending from the proximal end of housing 36 is a power cord 46 having a plug 48 which is adapted to be joined to a conventional RF voltage source (not shown) to energize the electrosurgical instrument. A power switch, generally designated 50, controls voltage supply to the instrument in the known manner. For example, when knob 52 is positioned at proximal location 54, the instrument is turned off, but when it is positioned distally (56, in shadow), it is turned on. Alternatively, it may be controlled by a conventional foot switch (FIG. 5). One or more ports 82 are disposed at the distal end of sheath 32 to moderate the amount of suction through the sleeve, as discussed more fully hereinafter.

FIG. 3 shows a plan, cross-sectional view of the electrosurgical instrument of FIG. 2. In this view, it is apparent that sheath 32 is generally tubular shaped, having a proximal end 58 and a distal end 60. Sheath 32 is preferably formed of semi-rigid plastic material. It is also apparent from this view that sheath 32 surrounds cylindrical rod 62. Rod 62 is preferably also formed from a rigid plastic and includes an insulating distal surface 64, having at least one electrode 66 extending therefrom. Electrode 66 is preferably a hook-shaped tungsten, tungsten alloy or stainless steel rod or tube, but its distal end may be formed in a variety of shapes, as disclosed in the co-pending application Ser. No. 07/728,337, assigned to applicant's assignee. A lumen 68 is molded, drilled or otherwise formed lengthwise through the rod to receive the straight leg portion 70 of the electrode 66, which is joined at its proximal end 72 to a wire 74. The wire 74 joins electrode 66 to switch 50 and, thus, to RF power (not shown). Rod 62 further includes a suction and/or irrigation lumen 76 which extends the full length of the rod 62. At the distal end of suction/irrigation lumen 76 is an entry/exit port 78.

At its proximal end, the irrigation/aspiration lumen 76 is joined to a tubular fluid delivery lumen 80, which extends to a fluid source (not shown). This same source can also be used as a reservoir to collect aspirate.

Positioned near the distal end of sheath 32 is at least one pressure relief port 82. Although a preferred placement that would suffice for most applications requires that two of these ports be placed at a radial distance of about 180°, it is envisioned that as few as one port or as many as permitted without compromising the structural integrity of the sheath 32 may be required for some applications. It is suggested that these ports have a diameter of approximately 30/1000 of an inch, although one skilled in the art will recognize that the particular application will determine the desirable port size and number. The ports 82 provide relief so that suction is not applied to the surrounding tissue with too much force, causing tissue damage by grasping the tissue too strongly.

In the view of FIG. 3, the internal construction of extender member 34 becomes apparent. Its cylindrical internal surface 84 further includes voids 86 and 88 dimensioned for receiving detents 90 and 92. In a retracted, proximal position, void 86 mates with detent 90 and void 88 mates with detent 92. In an extended, distal position, void 86 mates with detent 92 and void 88 is not occupied. An O-ring 94 of rubber or other elastomeric material provides a pneumatic seal between sheath 32 and rod 62. Preferably, the O-ring 94 is positioned at the distal end of rod 62 to prevent leakage toward extender member 34.

FIG. 4 is included to demonstrate that the irrigation/aspiration sheath of the present invention may be used with most commonly practiced tip embodiments. In particular, a pair of bipolar electrodes 96 and 98 are shown encompassed within sleeve or sheath 100 and joined to conductors 102 and 104. Sleeve or sheath 100 is analogous in construction to sheath 32. In this embodiment, irrigation/aspiration port 106 is positioned at the distal end of lumen 108. Lumen 108 mates with a fluid delivery means, in a manner similar to the embodiments of FIGS. 2 and 3.

In operation, the extender member 34 is advanced distally until detent 92 is locked within void 86, and electrode 66 is surrounded and shielded by distal end 60 of the sheath. This end is then inserted into a laparoscopic trocar or endoscope until it is positioned within a body region to be treated. Prior to application of RF voltage to electrode 66 as previously described, the sheath 32 must first be retracted, as at 42 in FIG. 2, whereupon detent 90 is locked within void 86. After tissue has been electrosurgically treated and it is desired to, for example, flush the treatment region to remove debris, the extender member 34 is again moved distally, causing sheath 32 to encompass electrode 66. Fluid is withdrawn from a reservoir (not shown) and projected through tubular fluid delivery lumen 80 and through lumen 76, then emitted through port 78, whereupon it flows freely through the treatment region.

It is frequently desired at this time to aspirate the flush fluid from the region. Fluid delivery lumen 80 is then connected to a suction source (not shown), Whereupon flush fluid and debris is withdrawn into the distal end 60 of sheath 32, and through port 78, lumen 76, and tubular fluid delivery means 80 into a conventional reservoir (not shown). The sheath 32 may then be withdrawn by proximal movement of extender member 34 to once again expose the electrode 66 to enable further electrosurgery.

In applications such as those previously described, one skilled in the art will recognize that in addition to regulating the degree of suction applied to a treatment region, the ports 82 also aid in dispersal of flush fluid as it exits the irrigation/aspiration port 78.

FIG. 5 shows a cross-sectional view of an alternative embodiment of the present invention, generally designated 110. As with the embodiment of FIGS. 2 through 4, it may be included on a monopolar or a bipolar instrument. A rigid plastic protective sleeve 112, having a distal end 114 and a proximal end 116, is secured to a housing 118. A cylindrical rod 120 supports at least one electrode 122, which extends from the rod at a distal surface 124. At its proximal end, the rod 120 is joined to an extender member 126. Distal movement of the extender member 126 within slot 128 shifts the proximal end of the rod 120 from a proximal position 130 to a distal position 132, until the distal surface 124 aligns with the opening 134 at the distal end 114 of the sleeve, thus enabling electrode 122 to protrude from within sleeve 112.

The electrode 122 may be formed from tungsten, tungsten alloy, or a curved stainless steel rod or tube, which is inserted into a lumen 136 drilled or otherwise formed lengthwise within rod 120. As described previously for the embodiment of FIGS. 2 through 4, the electrode 122 is likewise joined at 138 to a conductive wire 140. Wire 140 is joined to power supply cord 142, leading to a source of RF voltage 144. Power supply may be controlled by a conventional foot switch 146, or by a hand switch (not shown), as described in reference to FIG. 2. An irrigation/aspiration lumen 148 is also drilled or formed lengthwise through rod 120 from an open end 150. The proximal end of lumen 148 is joined to a tubular fluid duct 152, connected to a container 154, which may alternatively be a fluid reservoir or an aspirate receptacle. An elastomeric O-ring 156 prevents leakage between rod 120 and sleeve 112. Preferably, O-ring 156 is formed from silicone rubber.

The electrosurgical instrument of the present invention can be fabricated from a variety of available materials. For example, various medical grade plastics may be employed in molding the housings 36 and 118, with polycarbonate being preferred. The tubular sleeves 32 and 112 may be extruded polyethylene, polyurethane, polypropylene or Teflon®, with Teflon being preferred. The electrode conductors 74, 102, 104 and 140 are preferably formed from braided strands of stainless steel, although other materials may be used as well. They may be isolated from one another in traversing the length of the rods 62 and 120, but if not isolated, they must themselves be coated with an insulator.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. An electrosurgical instrument comprising:
   (a) an elongated tubular member having proximal end, a distal end and a lumen extending therebetween;
   (b) electrode means affixed to said distal end of said tubular member and projecting distally therefrom for electrosurgical cutting of tissue;
   (c) means for creating a suction force at the distal end of said elongated tubular member by applying a negative pressure at the proximal end of said lumen; and
   (d) means for selectively extending said suction force beyond said distal end of said elongated tubular member comprising a tubular sheath having a distal end coaxially disposed relative to said elongated tubular member, and a means for retracting said elongated tubular member from a first position wherein said electrode means is exposed and projects distally relative to said distal end of the sheath, to a second position wherein said electrode means is retracted to lie in covered relation to said sheath, said tubular sheath including at least one pressure relief port.

2. The electrosurgical instrument as in claim 1, wherein said tubular sheath is effectively pneumatically sealed relative to said tubular member.

3. The electrosurgical instrument as in claim 1, further including:
   a hand switch means for controlling a supply of an RF voltage to said electrode means.

4. The electrosurgical instrument as in claim 1, further including:
   a foot switch means for controlling a supply of an RF voltage to said electrode means.

5. The instrument as specified in claim 1 wherein the electrode means is retracted a predetermined distance from said distal end of said tubular sheath when said tubular member is retracted to said second position.

6. An electrosurgical instrument, comprising:
   (a) a housing means for grasping by a surgeon, said housing having a distal end and a proximal end;
   (b) a rod means for supporting an electrode, said rod means having a distal end and a proximal end and a first lumen extending therebetween;
   (c) at least one electrode means for cutting tissue having a proximal end inserted into said first lumen at said distal end of said rod means and extending distally therefrom;
   (d) an irrigation and aspiration lumen having a distal end and a proximal end and disposed within said rod means between said distal end and said proximal end of the rod means;
   (e) a sheath means for protecting said electrode, said sheath means having a distal end and a proximal end and coaxially disposed about said rod means, wherein said proximal end of the sheath means is affixed to said distal end of the housing; and
   (f) wherein said rod means is moveable from a first position wherein said distal end of the sheath means is in covering relation to said electrode means, to a second position wherein said distal end of said rod means is extended to expose said electrode means beyond said distal end of the sheath means.

7. The electrosurgical instrument as in claim 6, wherein said tubular sheath means is effectively pneumatically sealed relative to said rod means.

8. The electrosurgical instrument as in claim 6, further including:

at least one pressure release port disposed along said sheath means.

9. The electrosurgical instrument as in claim 6, further including:
   a hand switch means for controlling a supply of an RF voltage to said electrode means.

10. The electrosurgical instrument as in claim 6, further including:
    a foot switch means for controlling a supply of an RF voltage to said electrode means.

11. The instrument as specified in claim 6 wherein the distal end f said sheath means extends a predetermined distance beyond said electrode means when said rod means is in said first position.

12. An electrosurgical instrument comprising:
    (a) housing means for grasping by a surgeon including a rod means for supporting an electrode, said rod means having a distal end and a proximal end and a first and second lumen extending therebetween, wherein said proximal end of said rod means is affixed to said distal end of said housing means;
    (b) at least one electrode means for cutting tissue having a proximal end inserted at said distal end of said rod means into said first lumen and extending distally therefrom; and
    (c) a sheath means for protecting said electrode, said sheath means having a distal end and a proximal end and coaxially disposed about said rod means, said sheath means being moveable from a first secured position wherein said sheath means extends beyond and is in covering relation to said electrode means to a second secured position wherein said electrode means extends beyond said distal end of the sheath means and is exposed, wherein said housing means has a first detent means and said sheath means has a second detent means releasably securable to said first detent means to selectively allow said sheath means to longitudinally slide along said rod between said first and second secured positions.

13. The instrument as specified in claim 12 wherein one of said detent means comprises a protrusion and said other of said detent means comprises of at least a pair of conforming recesses.

14. The instrument as specified in claim 12, wherein said sheath means further comprises at least one pressure relief port.

15. The instrument of claim 1, 6 or 12 wherein said electrode means comprises a pair of electrodes.

* * * * *

UNITED STATES PATENT AND TRADEMARK OFFICE
CERTIFICATE OF CORRECTION

PATENT NO. : 5,197,963

DATED : March 30, 1993

INVENTOR(S) : David J. Parins

It is certified that error appears in the above-identified patent and that said Letters Patent is hereby corrected as shown below:

Column 7, line 2, claim 11, after the words "distal end", "f" should be changed to --of--.

Signed and Sealed this

Twenty-third Day of November, 1993

Attest:

BRUCE LEHMAN

Attesting Officer

Commissioner of Patents and Trademarks